(12) United States Patent
Akbarpour et al.

(10) Patent No.: US 10,833,409 B2
(45) Date of Patent: Nov. 10, 2020

(54) DUAL-BAND MAGNETIC ANTENNA

(71) Applicants: Alireza Akbarpour, Marvdasht (IR);
Somayyeh Chamaani, Tehran (IR)

(72) Inventors: Alireza Akbarpour, Marvdasht (IR);
Somayyeh Chamaani, Tehran (IR)

(*) Notice: Subject to any disclaimer, the term of this patent is extended or adjusted under 35 U.S.C. 154(b) by 38 days.

(21) Appl. No.: 16/214,390

(22) Filed: Dec. 10, 2018

(65) Prior Publication Data

US 2019/0109380 A1    Apr. 11, 2019

Related U.S. Application Data

(60) Provisional application No. 62/597,430, filed on Dec. 12, 2017.

(51) Int. Cl.
| | | |
|---|---|---|
| *H01Q 7/00* | (2006.01) | |
| *H01Q 5/328* | (2015.01) | |
| *H01Q 1/48* | (2006.01) | |
| *H04B 1/3827* | (2015.01) | |
| *A61B 5/00* | (2006.01) | |
| *H04B 1/00* | (2006.01) | |
| *H01Q 5/50* | (2015.01) | |
| *H01Q 5/371* | (2015.01) | |

(52) U.S. Cl.
CPC ............ *H01Q 5/328* (2015.01); *A61B 5/0031* (2013.01); *H01Q 1/48* (2013.01); *H01Q 5/371* (2015.01); *H01Q 5/50* (2015.01); *H01Q 7/00* (2013.01); *H04B 1/0064* (2013.01); *H04B 1/385* (2013.01); *A61B 2560/0209* (2013.01)

(58) Field of Classification Search
CPC . A61B 2560/0209; A61B 5/00; A61B 5/0031; H01Q 1/38; H01Q 1/48; H01Q 5/32; H01Q 5/328; H01Q 7/00; H01Q 5/371; H01Q 5/50; G01R 31/28; G01R 31/2836; H01L 21/268; H01L 21/67115; H01L 21/67259; H01L 22/12; H01L 23/544; H04B 1/00; H04B 1/38; H04B 1/3827
See application file for complete search history.

(56) References Cited

U.S. PATENT DOCUMENTS

| | | | | |
|---|---|---|---|---|
| 2,250,370 | A * | 7/1941 | Grimes | H03J 5/242 455/277.1 |
| 3,588,905 | A * | 6/1971 | Dunlavy, Jr. | H01Q 7/00 343/856 |
| 5,280,296 | A * | 1/1994 | Tan | H01Q 7/08 343/718 |
| 5,557,293 | A * | 9/1996 | McCoy | H01Q 1/242 343/702 |
| 7,439,933 | B2 * | 10/2008 | Uesaka | H01Q 1/22 235/492 |
| 8,077,116 | B2 * | 12/2011 | Shamblin | H01Q 1/243 343/895 |

* cited by examiner

*Primary Examiner* — Tho G Phan
(74) *Attorney, Agent, or Firm* — Bajwa IP Law Firm; Haris Zaheer Bajwa

(57) ABSTRACT

A magnetic antenna is disclosed. The magnetic antenna includes a dual-band magnetic antenna. The dual-band magnetic antenna includes a first magnetic loop and a second magnetic loop. The first magnetic loop is associated with a first frequency band, and the second magnetic loop is associated with a second frequency band.

20 Claims, 3 Drawing Sheets

DUAL-BAND MAGNETIC ANTENNA

CROSS-REFERENCE TO RELATED APPLICATION

This application claims the benefit of priority from U.S. Provisional Patent Application Ser. No. 62/597,430, filed on Dec. 12, 2017, and entitled "DUAL BAND IMPLANTABLE ANTENNA," which is incorporated herein by reference in its entirety.

TECHNICAL FIELD

The present disclosure generally relates to network communications, and particularly, to dual-band antennas.

BACKGROUND

Implant systems have been propounded in recent years for both health-care monitoring and medical procedures, including heart stimulation, capsule endoscopy, and drug delivery. Due to placement into a human body, power consumption is a bottleneck of these systems. To increase the lifetime of the battery, event-driven devices with a wake-up signal have been utilized. Dual-band antennas in both implant and base station sides may be utilized for this purpose.

Dual-band antennas may be utilized to provide two frequency bands for both data processing and wake-up control. However, dimensions of this type of antennas may not be small enough for implant applications. Moreover, decreasing the size of these antennas may lead to high specific absorption rates (SAR), which may harm biological tissues. There is, therefore, a need for a dual-band antenna with a small size and low SAR.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary magnetic antenna. An exemplary magnetic antenna may include a dual-band magnetic antenna. In an exemplary embodiment, the dual-band magnetic antenna may include a first magnetic loop and a second magnetic loop. The first magnetic loop may be associated with a first frequency band, and the second magnetic loop may be associated with a second frequency band. In an exemplary embodiment, the first frequency band may include a medical implant communication system (MICS) band, and the second frequency band may include an industrial, scientific and medical (ISM) band. In an exemplary embodiment, the first magnetic loop may include a single band electrically coupled loop antenna (ECLA).

In an exemplary embodiment, the first magnetic loop may include a ground plane with a length L and a width W, a first vertical plane with a height h and the width W, a first horizontal plane with the length L and the width W, second vertical plane with a height h' and the width W where h'<h, a second horizontal plane with a length $L_s$ and the width W where $L_S$<L, a third horizontal plane with a length $L_P$ and the width W, and a first lumped capacitor with a capacitance $C_1$. A first end of the first vertical plane may be attached to an end of the ground plane. In an exemplary embodiment, the first vertical plane may be perpendicular to the ground plane. A first end of the first horizontal plane may be attached to a second end of the first vertical plane. In an exemplary embodiment, the first horizontal plane may be parallel with the ground plane. A first end of the second vertical plane may be attached to a second end of the first horizontal plane and a second end of the second vertical plane may be located at a distance $t_S$ from the ground plane, where $t_S$=h−h'. In an exemplary embodiment, the second vertical plane may be parallel with the first vertical plane. A first end of the second horizontal plane may be attached to a second end of the second vertical plane and a second end of the second horizontal plane may be located at a distance $t_h$ from the first vertical plane, where $t_h$=L−$L_S$. In an exemplary embodiment, the second horizontal plane may be parallel with the ground plane, and may include a hole. The third horizontal plane may be parallel with the ground plane, and may be located at a distance $t_p$ from the second horizontal plane and a distance $t_g$ from the ground plane, where $t_g$=$t_P$+$t_S$. In an exemplary embodiment, the third horizontal plane may be coupled with the ground plane via a feeding port through the hole. The first lumped capacitor may be connected between the ground plane and the third horizontal plane.

In an exemplary embodiment, the second magnetic loop may include a fourth horizontal plane with a length $L_I$ and the width W, a third vertical plane with a height $h_I$ and the width W, and a second lumped capacitor with a capacitance $C_2$. In an exemplary embodiment, a first end of the fourth horizontal plane may be attached to the second vertical plane and the second end of the fourth horizontal plane may be located at a distance $t_I$ from the first vertical plane, where $t_I$=L−$L_I$. In an exemplary embodiment, the fourth horizontal plane may be parallel with the ground plane, and may be located at a distance $t_I$ from the ground plane. In an exemplary embodiment, a first end of the third vertical plane may be attached to the second end of the fourth horizontal plane and a second end of the third vertical plane may be located at a distance $t_v$ from the ground plane, where $t_v$<$t_I$. In an exemplary embodiment, the fourth horizontal plane may be parallel with the first vertical plane, and the second lumped capacitor may be connected between the ground plane and the second end of the fourth horizontal plane.

In an exemplary embodiment, the length L, the width W, the height h, the length $L_S$, the distance $t_s$, the distance $t_p$, and the capacitance $C_1$ may be set based on the first frequency band, and the length $L_I$, the width W, the height $h_I$, the distance $t_I$, and the capacitance $C_2$ may be set based on the second frequency band.

In an exemplary embodiment, the length L may be in a range of 4 mm and 6 mm, the width W may be in a range of 2.4 mm and 3.6 mm, the height h may be in a range of 4 mm and 6 mm, the length $L_S$ may be in a range of 2.8 mm and 4.2 mm, the distance $t_s$ may be in a range of 0.6 mm and 0.9 mm, the distance $t_p$ may be in a range of 0.16 mm and 0.24 mm, the capacitance $C_1$ may be in a range of 21 pF and 32 pF, the distance $t_v$ may be equal to the distance $t_S$, the length $L_I$ may be in a range of 3.6 mm and 5.4 mm, the height $h_I$ may be in a range of 0.6 mm and 0.9 mm, and the capacitance $C_2$ may be in a range of 3.55 pF and 3.4 pF.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary dual-band magnetic antenna. An exemplary antenna may include two magnetic loops, each for a separate frequency band. Incorporating the two magnetic loops in the dual-band magnetic antenna may result in decreasing the antenna dimensions. Accordingly, an exemplary dual-band magnetic antenna with its smaller size compared to conventional dual-band antennas allows for its use in bio-implant applications due to its low disturbance on patients' comfort.

Figure 1:
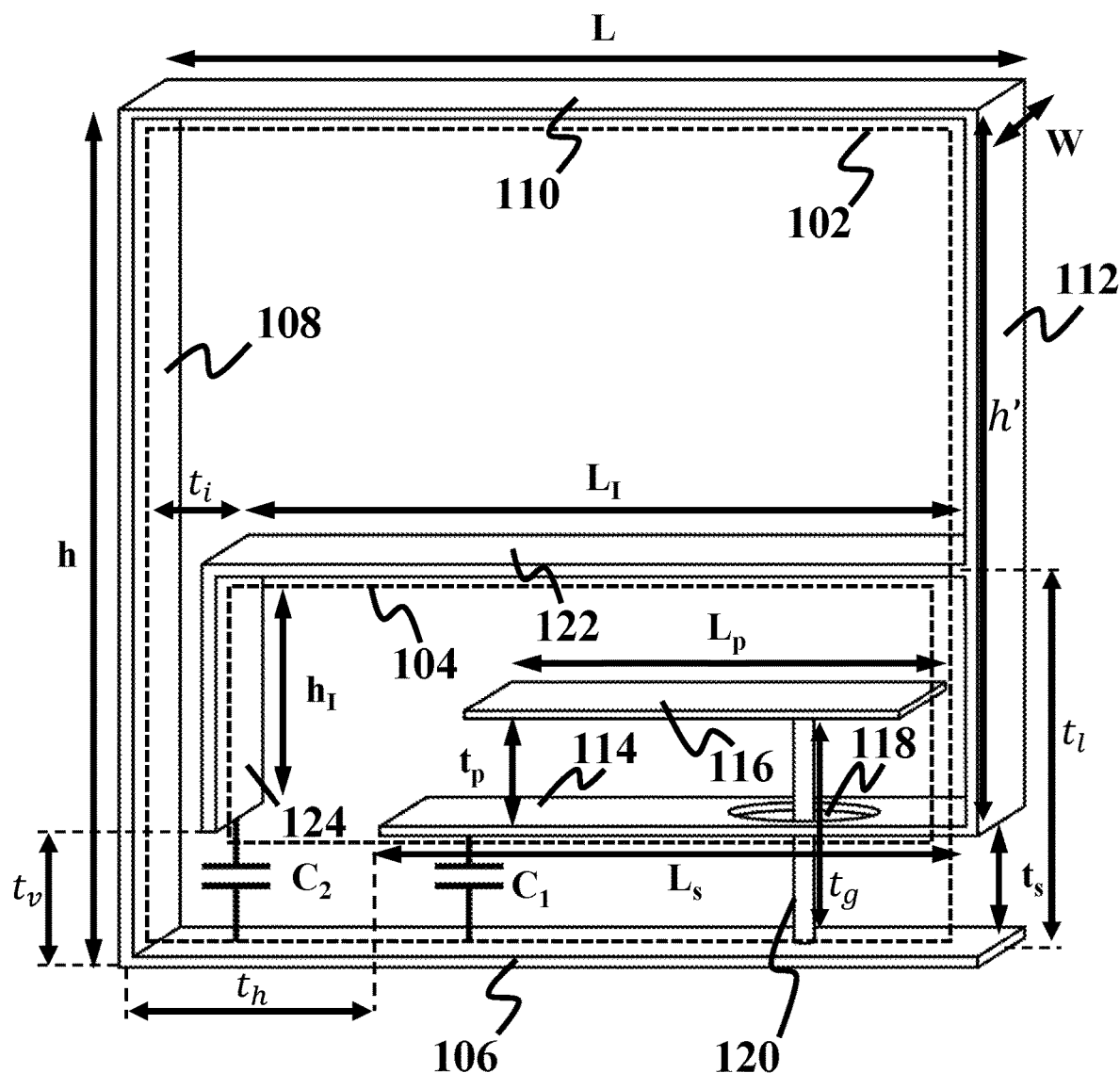
FIG. 1 shows a schematic of an exemplary magnetic antenna, consistent with one or more exemplary embodiments of the present disclosure.

FIG. 1 shows a schematic of an exemplary magnetic antenna, consistent with one or more exemplary embodiments of the present disclosure. In an exemplary embodiment, an exemplary magnetic antenna 100 may include a dual-band magnetic antenna. In an exemplary embodiment, the dual-band magnetic antenna may include a first magnetic loop 102 and a second magnetic loop 104. In an exemplary embodiment, first magnetic loop 102 may be associated with a first frequency band, and second magnetic loop 104 may be associated with a second frequency band. In an exemplary embodiment, the first frequency band may be determined based on a size of first magnetic loop 102, and the second frequency band may be determined based on a size of second magnetic loop 104. In an exemplary embodiment, the first frequency band may include a medical implant communication system (MICS) band, which is dedicated to data transmission between the antenna and a base station, and the second frequency band may include an industrial, scientific and medical (ISM) band, which is dedicated to wake-up signals. In an exemplary embodiment, wake-up signals may refer to external commands received by the antenna, which may activate implanted biosensors to start sending or receiving data from the base station. As a result, utilizing the first frequency band and the second frequency band may lead to the dual-band operation, which may extend a battery lifetime of magnetic antenna 100, making it useful in both implant and off-body applications. In an exemplary embodiment, first magnetic loop 102 may include a single band electrically coupled loop antenna (ECLA), which has low near zone electric field and specific absorption rate (SAR).

In an exemplary embodiment, first magnetic loop 102 may include a ground plane 106 with a length L and a width W, a first vertical plane 108 with a height h and width W, a first horizontal plane 110 with length L and width W, second vertical plane 112 with a height h' and width W where h'<h, a second horizontal plane 114 with a length $L_S$ and width W where $L_S$<L, a third horizontal plane 116 with a length $L_P$ and width W, and a first lumped capacitor $C_1$. In an exemplary embodiment, a first end of first vertical plane 108 may be attached to an end of ground plane 106. In an exemplary embodiment, first vertical plane 108 may be perpendicular to ground plane 106.

In an exemplary embodiment, a first end of first horizontal plane 110 may be attached to a second end of first vertical plane 108. In an exemplary embodiment, first horizontal plane 110 may be parallel with ground plane 106. A first end of second vertical plane 112 may be attached to a second end of first horizontal plane 110 and a second end of second vertical plane 112 may be located at a distance $t_S$ from ground plane 106, where $t_S$=h−h'. In an exemplary embodiment, second vertical plane 112 may be parallel with first vertical plane 108.

In an exemplary embodiment, a first end of second horizontal plane 114 may be attached to a second end of second vertical plane 112 and a second end of second horizontal plane 114 may be located at a distance $t_h$ from first vertical plane 108, where $t_h$=L−$L_S$. In an exemplary embodiment, second horizontal plane 114 may be parallel with ground plane 106, and may include a hole 118.

In an exemplary embodiment, third horizontal plane 116 may be parallel with ground plane 106, and may be located at a distance $t_p$ from second horizontal plane 114 and a distance $t_g$ from ground plane 106, where $t_g$=$t_p$+$t_S$. In an exemplary embodiment, third horizontal plane 116 may be coupled with ground plane 106 via a feeding port 120 through hole 118. In an exemplary embodiment, first lumped capacitor $C_1$ may be connected between ground plane 106 and third horizontal plane 116. A resonance frequency of first magnetic loop 102 is decreased by increasing the capacitance of first lumped capacitor $C_1$. Since the resonance frequency is increased by reducing the antenna size, to achieve a given value of the resonance frequency for first magnetic loop 102 with a reduced size, the capacitance of first lumped capacitor $C_1$ may be increased to compensate the impact of the reduced size of first magnetic loop 102. Therefore, in an exemplary embodiment, first magnetic loop 102 may be miniaturized by using first lumped capacitor $C_1$.

In an exemplary embodiment, first magnetic loop 102 may be a short-circuited high impedance transmission line, which is fed by a capacitive coupling and a distributed capacitor. This configuration (combination of the high impedance transmission line as an inductor and the distributed capacitor) mimics a distributed LC resonator wherein its resonance frequency is determined by first magnetic loop 102 dimensions (L, W, and h) and the distributed capacitance between first magnetic loop 102 and ground plane 106 ($t_S$, W, and $L_S$). The input impedance may be tuned by feed head dimensions ($t_p$, W, and $L_p$).

In an exemplary embodiment, second magnetic loop 104 may include a fourth horizontal plane 122 with a length $L_I$ and width W, a third vertical plane 124 with a height $h_I$ and width W, and a second lumped capacitor $C_2$. In an exemplary embodiment, a first end of fourth horizontal plane 122 may be attached to second vertical plane 112 and the second end of fourth horizontal plane 122 may be located at a distance $t_I$ from first vertical plane 108, where $t_I$=L−$L_I$. In an exemplary embodiment, fourth horizontal plane 122 may be parallel with ground plane 106, and may be located at a distance $t_I$ from ground plane 106.

In an exemplary embodiment, a first end of third vertical plane 124 may be attached to the second end of fourth horizontal plane 122 and a second end of third vertical plane 124 may be located at a distance $t_v$ from ground plane 106, where $t_v$<$t_I$. In an exemplary embodiment, fourth horizontal plane 122 may be parallel with first vertical plane 108, and second lumped capacitor $C_2$ may be connected between ground plane 106 and the second end of fourth horizontal plane 122. A resonance frequency of second magnetic loop 104 is decreased by increasing the capacitance of second lumped capacitor $C_2$. Since the resonance frequency is increased by reducing the antenna size, to achieve a given value of the resonance frequency for first magnetic loop 102 with a reduced size, the capacitance of second lumped capacitor $C_2$ may be increased to compensate the impact of the reduced size of second magnetic loop 104. Therefore, second magnetic loop 104 may be miniaturized by using second lumped capacitor $C_2$. Consequently, second magnetic loop 104 may be a short-circuited high impedance transmission line with a capacitive coupling.

In an exemplary embodiment, length L, width W, height h, length $L_s$, distance $t_s$, distance $t_p$, and the capacitance of first lumped capacitor $C_1$ may be set based on the first frequency band, and length $L_I$, width W, height $h_I$, distance $t_I$, and the capacitance of second lumped capacitor $C_2$ may be set based on the second frequency band.

In an exemplary embodiment, length L may be in a range of 4 mm and 6 mm, width W may be in a range of 2.4 mm and 3.6 mm, height h may be in a range of 4 mm and 6 mm, length $L_s$ may be in a range of 2.8 mm and 4.2 mm, distance $t_s$ may be in a range of 0.6 mm and 0.9 mm, distance $t_p$ may be in a range of 0.16 mm and 0.24 mm, capacitance $C_1$ may be in a range of 21 pF and 32 pF, distance $t_v$ may be equal to distance $t_s$, length $L_I$ may be in a range of 3.6 mm and 5.4 mm, height $h_I$ may be in a range of 0.6 mm and 0.9 mm, and the capacitance of second lumped capacitor $C_2$ may be in a range of 3.55 pF and 3.4 pF.

EXAMPLE

In this example, an exemplary implementation of magnetic antenna 100 for bio-implant applications is numerically investigated. The exemplary antenna uses lumped capacitors for miniaturization ($C_1 \approx 26.5$ pF, $C_2 \approx 2.84$ pF). The geometric parameters of the antenna are listed in Table 1. The bandwidth of the antenna is about 2.8 and 7.1 MHz for the MICS and ISM bands, respectively. In low power wireless implant sensor nodes, the typical data rate for wake-up codes is about 100 kb/s and the MICS band data rate is slower than about 300 Kb/s. Therefore, a few MHz bandwidth may be sufficient for both the ISM and the MICS bands. Hence, the exemplary magnetic antenna shows a very compact size, a low SAR with an adequate bandwidth, and an acceptable gain for bio-implant applications.

To enhance radiation efficiency and power transmission for bio-implant applications, an insulation layer may be added around the antenna to prevent metallic oxidation and short circuit effects due to the high conductivity of human body tissues. In this example, a Teflon insulation layer with a thickness of about 1 mm is added around exemplary implementation of magnetic antenna 100.

Since the operating frequency of the MICS band is significantly smaller than that of the ISM band, the MICS band may impose a lower limit on the antenna dimensions. Therefore, the design procedure starts with the MICS band radiator. The resonance frequency of the MICS band is tuned using the parameters of a single band ECLA (L, W, h, $C_1$, $L_S$). The increment of these parameters leads to the increment of either an inductance or a capacitance of an equivalent distributed LC circuit, and consequently, the MICS band resonance frequency decreases.

Figure 2:
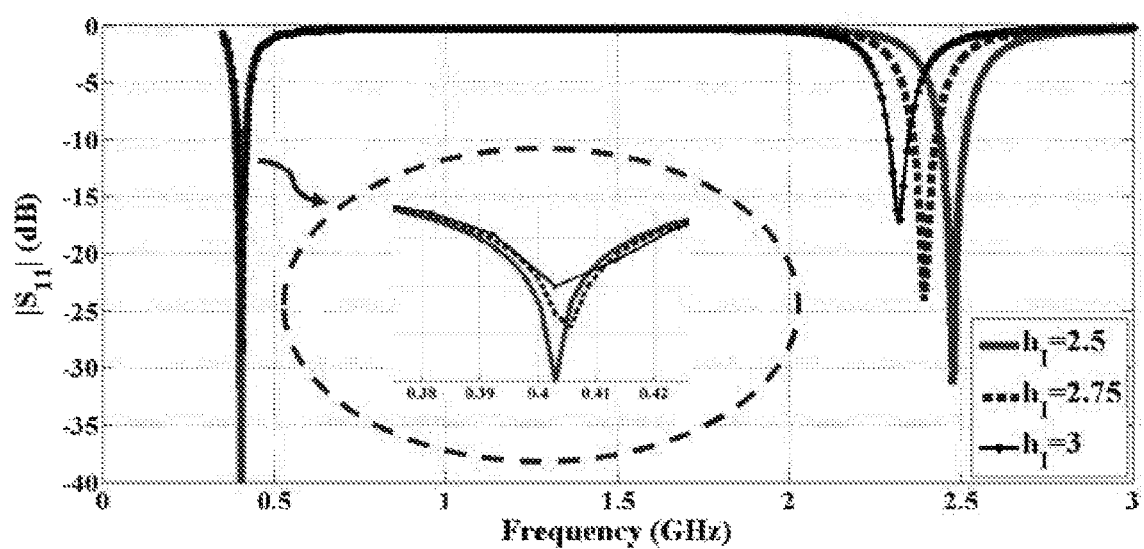
FIG. 2 shows an effect of variations of a height $h_I$ of a vertical plane of an exemplary dual-band magnetic antenna on a resonance frequency of an industrial, scientific and medical (ISM) band, consistent with one or more exemplary embodiments of the present disclosure.

FIG. 2 shows the effect of variations of height $h_I$ of third vertical plane 124 on the resonance frequency of the ISM band, consistent with one or more exemplary embodiments of the present disclosure. As shown in FIG. 2, increasing $h_i$ increases the inductance and decreases the capacitance of the distributed LC circuit in the ISM band. However, the inductance increment dominates the capacitance decrement, and consequently the resonance frequency of ISM band decreases.

Figure 3:
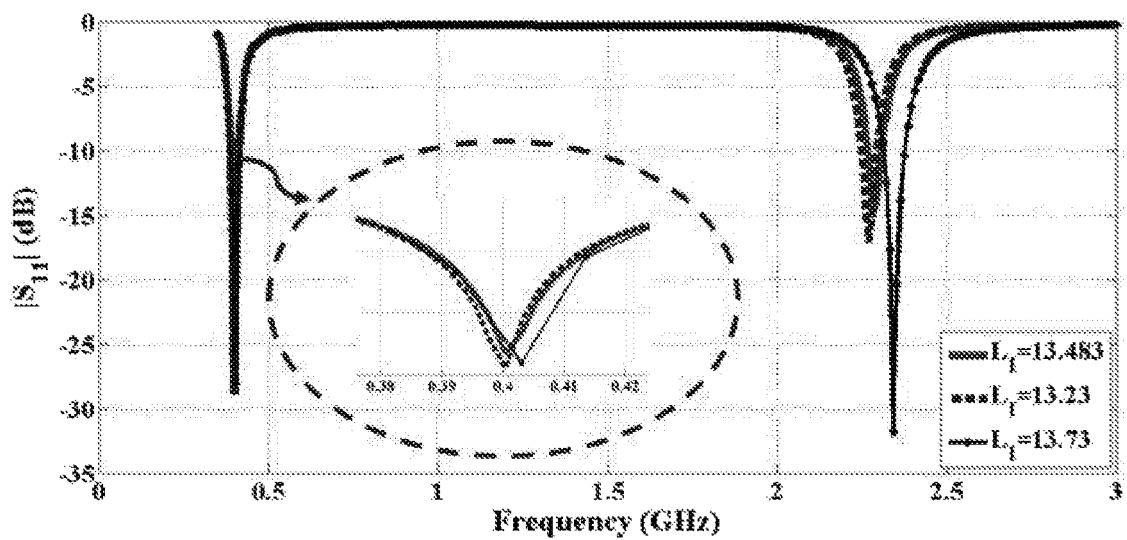
FIG. 3 shows an effect of variations of a length of a horizontal plane of an exemplary dual-band magnetic antenna on a resonance frequency of an ISM band, consistent with one or more exemplary embodiments of the present disclosure.

FIG. 3 shows the effect of variations of length $L_I$ of fourth horizontal plane 122 on the resonance frequency of the ISM band, consistent with one or more exemplary embodiments of the present disclosure. As shown in FIG. 3, variation of $L_I$ has a non-monotonic effect on the ISM band resonance frequency.

TABLE 1

Approximate values of geometric parameters of an exemplary magnetic antenna.

| Parameter | Value (mm) |
| --- | --- |
| L | 5 |
| W | 3 |
| h | 5 |
| $L_s$ | 3.5 |
| $t_s$ | 0.75 |
| $L_P$ | 3.7 |
| $L_I$ | 4.51 |
| $h_I$ | 0.76 |
| $t_p$ | 0.2 |
| Teflon thickness | 1 |

Length $L_S$ of second horizontal plane 114 is an effective parameter on the resonance frequency, as decreasing it increases both the MICS and ISM resonance frequencies. Therefore, if $L_S$ is used for tuning the ISM band resonance frequency, the MICS band resonance frequency detuning should be compensated by other parameters such as h or $C_1$.

In both frequency bands impedance matching is done by tuning the feeding head parameters ($L_p$, $t_p$, and $W_p$) and the feed position.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A dual-band magnetic antenna, comprising:
   a first magnetic loop, comprising:
      a ground plane with a length L and a width W;
      a first vertical plane with a height h and the width W, a first end of the first vertical plane attached to an end of the ground plane, the first vertical plane perpendicular to the ground plane;
      a first horizontal plane with the length L and the width W, a first end of the first horizontal plane attached to a second end of the first vertical plane, the first horizontal plane parallel with the ground plane;
      a second vertical plane with a height h' and the width W, where h'<h, a first end of the second vertical plane attached to a second end of the first horizontal plane and a second end of the second vertical plane located at a distance $t_s$ from the ground plane, where $t_s$=h–h', the second vertical plane parallel with the first vertical plane;
      a second horizontal plane with a length $L_s$ and the width W, where $L_s$<L, a first end of the second horizontal plane attached to a second end of the second vertical plane and a second end of the second horizontal plane located at a distance $t_h$ from the first vertical plane, where $t_h$=L–$L_s$, the second horizontal plane parallel with the ground plane, the second horizontal plane comprising a hole;
      a third horizontal plane with a length $L_p$ and the width W, the third horizontal plane parallel with the ground plane, the third horizontal plane located at a distance $t_p$ from the second horizontal plane and a distance $t_9$ from the ground plane, where $t_9$=$t_p$+$t_s$, the third horizontal plane coupled with the ground plane via a feeding port through the hole; and
      a first lumped capacitor with a capacitance $C_1$ connected between the ground plane and the third horizontal plane; and
   a second magnetic loop, comprising:
      a fourth horizontal plane with a length $L_I$ and the width W, a first end of the fourth horizontal plane attached to the second vertical plane and the second end of the fourth horizontal plane located at a distance $t_i$ from the first vertical plane, where $t_i$=L–$L_I$, the fourth horizontal plane parallel with the ground plane, the fourth horizontal plane located at a distance $t_I$ from the ground plane;

a third vertical plane with a height $h_I$ and the width W, a first end of the third vertical plane attached to the second end of the fourth horizontal plane and a second end of the third vertical plane located at a distance $t_v$ from the ground plane, where $t_v < t_1$, the fourth horizontal plane parallel with the first vertical plane; and a second lumped capacitor with a capacitance $C_2$ connected between the ground plane and the second end of the fourth horizontal plane.

2. A magnetic antenna, comprising a dual-band magnetic antenna, the dual-band magnetic antenna comprising a first magnetic loop associated with a first frequency band, the first magnetic loop comprising:

a ground plane with a length L and a width W;

a first vertical plane with a height h and the width W, a first end of the first vertical plane attached to an end of the ground plane, the first vertical plane perpendicular to the ground plane;

a first horizontal plane with the length L and the width W, a first end of the first horizontal plane attached to a second end of the first vertical plane, the first horizontal plane parallel with the ground plane;

a second vertical plane with a height h' and the width W, where h'<h, a first end of the second vertical plane attached to a second end of the first horizontal plane and a second end of the second vertical plane located at a distance $t_s$ from the ground plane, where $t_s = h - h'$, the second vertical plane parallel with the first vertical plane; and a second horizontal plane with a length $L_s$ and the width W, where $L_s < L$, a first end of the second horizontal plane attached to a second end of the second vertical plane and a second end of the second horizontal plane located at a distance $t_h$ from the first vertical plane, where $t_h = L - L_s$, the second horizontal plane parallel with the ground plane, the second horizontal plane comprising a hole.

3. The magnetic antenna of claim 2, wherein the dual-band magnetic antenna further comprises a second magnetic loop associated with a second frequency band.

4. The magnetic antenna of claim 3, wherein the first magnetic loop comprises a single band electrically coupled loop antenna (ECLA).

5. The magnetic antenna of claim 3, wherein the first magnetic loop further comprises:

a third horizontal plane with a length $L_p$ and the width W, the third horizontal plane parallel with the ground plane, the third horizontal plane located at a distance $t_p$ from the second horizontal plane and a distance $t_g$ from the ground plane, where $t_g = t_p + t_s$, the third horizontal plane coupled with the ground plane via a feeding port through the hole; and a first lumped capacitor with a capacitance $C_1$ connected between the ground plane and the third horizontal plane.

6. The magnetic antenna of claim 5, wherein the second magnetic loop comprises:

a fourth horizontal plane with a length $L_I$ and the width W, a first end of the fourth horizontal plane attached to the second vertical plane and the second end of the fourth horizontal plane located at a distance $t_i$ from the first vertical plane, where $t_i = L - L_I$, the fourth horizontal plane parallel with the ground plane, the fourth horizontal plane located at a distance $t_I$ from the ground plane;

a third vertical plane with a height $h_I$ and the width W, a first end of the third vertical plane attached to the second end of the fourth horizontal plane and a second end of the third vertical plane located at a distance $t_v$ from the ground plane, where $t_v < t_I$, the fourth horizontal plane parallel with the first vertical plane; and a second lumped capacitor with a capacitance $C_2$ connected between the ground plane and the second end of the fourth horizontal plane.

7. The magnetic antenna of claim 6, wherein the length $L_I$, the width W, the height $h_I$, the distance $t_I$, and the capacitance $C_2$ are set based on the second frequency band.

8. The magnetic antenna of claim 6, wherein the distance $t_v$ is equal to the distance $t_s$.

9. The magnetic antenna of claim 6, wherein the length $L_I$ is in a range of 3.6 mm and 5.4 mm.

10. The magnetic antenna of claim 6, wherein the height $h_I$ is in a range of 0.6 mm and 0.9 mm.

11. The magnetic antenna of claim 6, wherein the capacitance $C_2$ is in a range of 3.55 pF and 3.4 pF.

12. The magnetic antenna of claim 5, wherein the length L, the width W, the height h, the length $L_s$, the distance $t_s$, the distance $t_p$, and the capacitance $C_1$ are based on the first frequency band.

13. The magnetic antenna of claim 5, wherein the length L is in a range of 4 mm and 6 mm.

14. The magnetic antenna of claim 5, wherein the width W is in a range of 2.4 mm and 3.6 mm.

15. The magnetic antenna of claim 5, wherein the height h is in a range of 4 mm and 6 mm.

16. The magnetic antenna of claim 5, wherein the length $L_s$, is in a range of 2.8 mm and 4.2 mm.

17. The magnetic antenna of claim 5, wherein the distance is $t_s$ in a range of 0.6 mm and 0.9 mm.

18. The magnetic antenna of claim 5, wherein the distance $t_p$ is in a range of 0.16 mm and 0.24 mm.

19. The magnetic antenna of claim 5, wherein the capacitance $C_1$ is in a range of 21 pF and 32 pF.

20. The magnetic antenna of claim 3, wherein the first frequency band comprises an industrial, scientific and medical (ISM) band, and the second frequency band comprises a medical implant communication system (MICS) band.

* * * * *